United States Patent [19]

Westbrook

[11] Patent Number: 5,010,896
[45] Date of Patent: Apr. 30, 1991

[54] PULSED GALVANIC STIMULATOR

[75] Inventor: Barbara-Ann Westbrook, Falls Church, Va.

[73] Assignee: Westec Corporation, Manassas, Va.

[21] Appl. No.: 422,532

[22] Filed: Oct. 17, 1989

[51] Int. Cl.⁵ .............................................. A61N 1/04
[52] U.S. Cl. ................................... 128/798; 128/802; 128/803
[58] Field of Search ............... 128/783, 791, 798, 799, 128/802, 803, 640, 644

[56] References Cited

U.S. PATENT DOCUMENTS

| 2,651,304 | 9/1953 | Browner | 128/798 |
| 3,534,727 | 10/1970 | Roman | 128/644 |
| 4,122,843 | 10/1978 | Zdrojkowski | 128/644 |
| 4,265,253 | 5/1981 | Abraham | 128/798 |
| 4,354,508 | 10/1982 | Murfitt et al. | 128/798 |
| 4,370,984 | 2/1983 | Cartmell | 128/803 |
| 4,381,012 | 4/1983 | Russek | 128/644 |

FOREIGN PATENT DOCUMENTS 2531330 2/1984 France ................................ 128/644

Primary Examiner—Lee S. Cohen
Attorney, Agent, or Firm—Foley & Lardner

[57] ABSTRACT

A pulsed galvanic medical treatment device is provided comprising a power control and supply source, a pair of electrodes connected to the power control and supply source, a return pad connected to the power control and supply source and connecting wraps for tightly strapping the electrodes and return pads to a portion of the body to be treated. The electrodes and return pads are formed from a liquid absorbing sponge member backed by a flexible vinyl coating and having an electrical conducting substance disposed therebetween. The electrical conductor extends beyond the electrodes and return pad at least several inches where it can be connected to the power control and supply source.

14 Claims, 2 Drawing Sheets

PULSED GALVANIC STIMULATOR

BACKGROUND OF THE INVENTION

1. Field of the Invention

This invention relates to devices for electrical muscle stimulation, and more particularly, to a pulsed galvanic medical treatment device for stimulating muscles.

2. Discussion of the Related Art

Pulsed galvanic stimulation therapy, sometimes called monophasic or pulsed DC therapy, has been found effective as a therapeutic adjunct for treating edema, muscle spasms, and sprains. It has also been used to influence local blood circulation and to maintain or increase range of motion.

Conventional pulse galvanic stimulators employ electrode pads consisting of liquid absorbing sponge material on one side backed by a layer of rubber or vinyl. These electrodes are strapped on opposite sides of a body part to be treated, such as an arm or knee. An electrically conducting return pad is applied to a nearby large muscle group of the body, and all three electrodes are connected to a power control and supply source.

Previous pulse galvanic stimulators have suffered from numerous disadvantages. First of all, the electrically conducting sponge material is backed by stiff rubber which is too stiff to bend over large muscle groups or to contour to smaller joints. Also, the connector which connects the electrode to the power control and supply source protrudes from the electrodes which makes it uncomfortable for a patient to sit or lie on and with repeated use the connector eventually pushes into the pad. Furthermore, with the connector located so near to the electrode, the patient has difficulty seeing the connection, and the risk of electrical shock is increased. Moreover, previous devices have been difficult to strap to the body, since typically more than two hands were required to tightly strap the electrodes to the body parts.

SUMMARY OF THE INVENTION

Accordingly, it is an object of the present invention to provide a pulse galvanic stimulator which can be easily contoured to different parts of the body.

A further object of the invention is to provide a galvanic stimulator having a connector which will not be uncomfortable to sit or lie on.

Another object of the invention is to provide a galvanic stimulator having a connector which is easy to see and safe to use.

Yet another object of the invention is to provide a pulse galvanic stimulator which can be easily and accurately placed by the clinician and or patient.

A further object of the invention is to provide a galvanic stimulator which can be tightly fastened to the body even by a patient with limited manual dexterity.

According to the present invention, the foregoing and additional objects are attained by providing a pulsed galvanic medical treatment device comprising a power control and supply source, a pair of electrodes connected to the power control and supply source, a return pad connected to the power control and supply source and connecting wraps for tightly strapping the electrodes and return pads to a portion of the body to be treated. The electrodes and return pads are formed from a liquid absorbing sponge member backed by a flexible vinyl coating and having an electrical conducting substance disposed therebetween. The electrical conductor extends beyond the electrodes and return pad at least several inches where it can be connected to the power control and supply source.

DETAILED DESCRIPTION OF THE PREFERRED EMBODIMENTS

Figure 1:
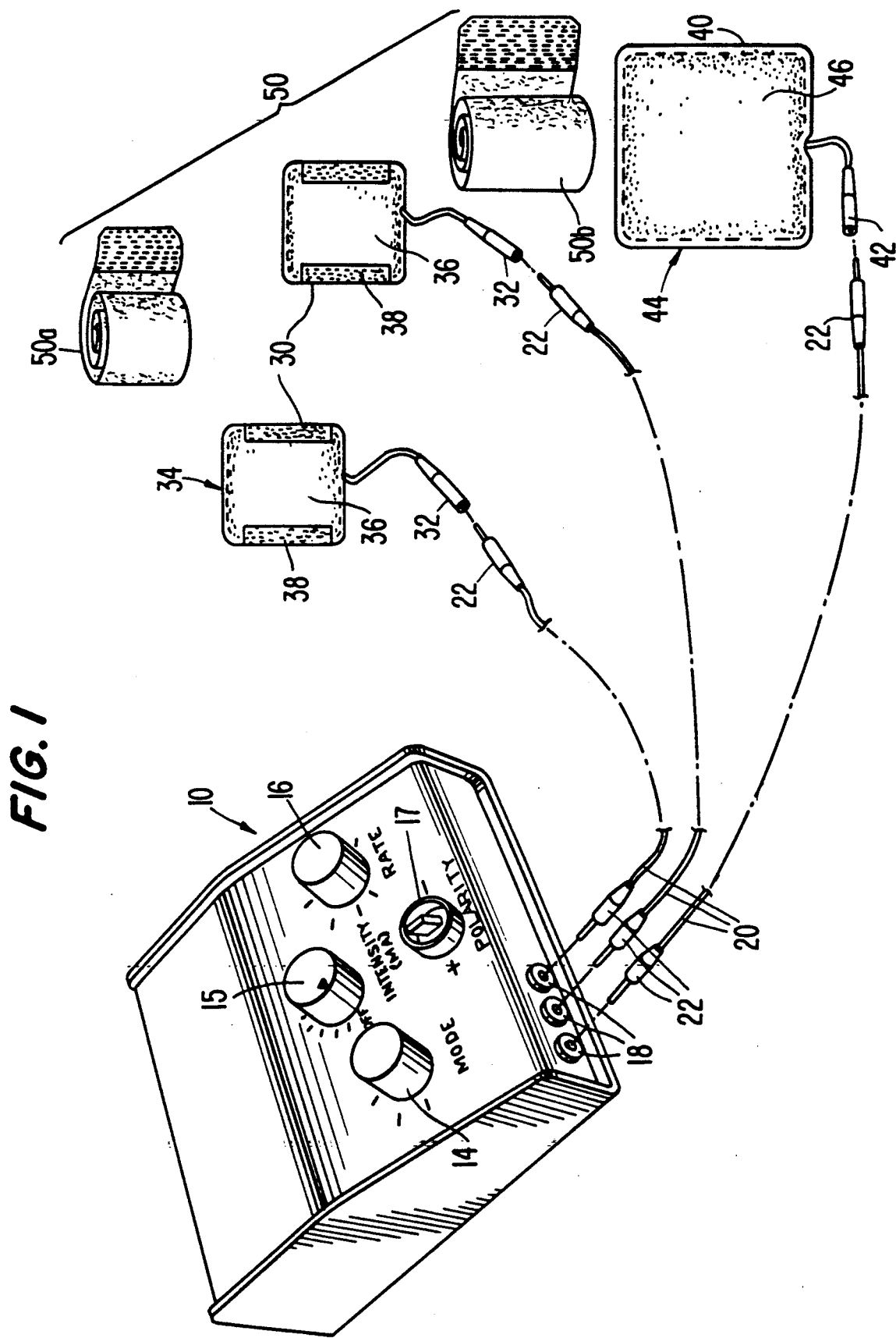
FIG. 1 is a perspective view of a disassembled pulse galvanic stimulator according to the present invention.

As illustrated in FIG. 1, the present invention comprehends a power control and supply source 10 which is connected via a plurality of wires 20 to a pair of electrode pads 30 and a return pad 40. A pair of connecting wraps 50 are used to secure the electrode pads 30 and return pad 40 to the portion of the body to be treated.

The power control and supply source 10 has a mode control 14 for selecting the mode of current delivery. The current can be set to alternate between the pair of electrode pads 30 at a predetermined interval. The mode control can also be set so that both pads are continuously active or set so that current is delivered for an interval and then turned off for an interval. An intensity control 15 turns the power control supply source on and off and adjusts the level of stimulation to the pair of electrode pads. A rate control 16 is used to vary the rate (or frequency) of current pulses. A polarity switch 17 selects the output polarity of the electrode treatment pads, either negative or positive whereby a return or dispersive pad becomes the opposite polarity. The power control supply source has a plurality of output jacks 18 for supplying power to the rest of the system. The output jacks 18 are connected to electrode pads 30 and return pad 40 via lead wires 20, each having a pair of corresponding connectors 22 disposed at opposite ends thereof. A male lead wire connector 22 is plugged into a respective pigtail connector 32 or 42 which communicates electrically with a conducting substrate disposed between a liquid absorbing member 34 and 44 of the electrode pads 30 and return pads 40, respectively. A flexible member 36, 46 forms the side of pads 30 and 40 opposite that of liquid absorbing member 34, 44. The vinyl backing has a pair of attachment tabs 38 for connecting the securing wrap 50. Especially beneficial results have been attained using hook and loop fasteners such as "VELCRO" ®, commercially available from E. I. DuPont deNemours & Co.

Figure 2:
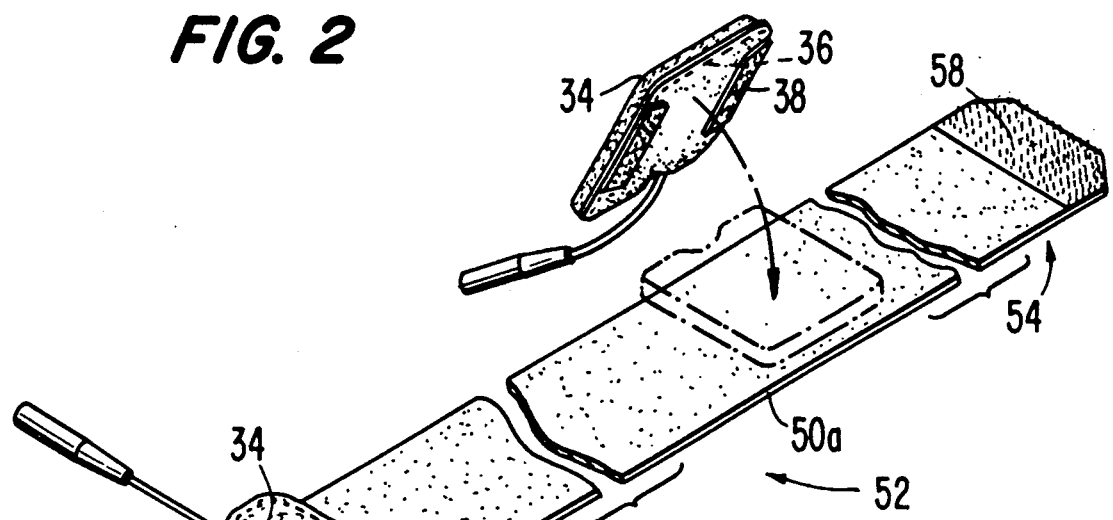
FIG. 2 is a perspective view of a pair of electrodes attached to the connecting wrap of the present invention.

Referring now to FIG. 2, there is shown the attachment of electrode pads 30 to a securing wrap 50a. The securing wrap 50a comprises a substantially inelastic base portion 52 forming a first end thereof and an elastic tightening portion 54 forming a second end thereof. The surface of the inelastic base portion 52 should be made of a material, such as polyester, which adheres well to the attaching tab 38. The securing wrap 50 has a starter tab 56 and a tightening tab 58 at either end thereof. These may also be made of hook and loop fastening material.

Figure 3:
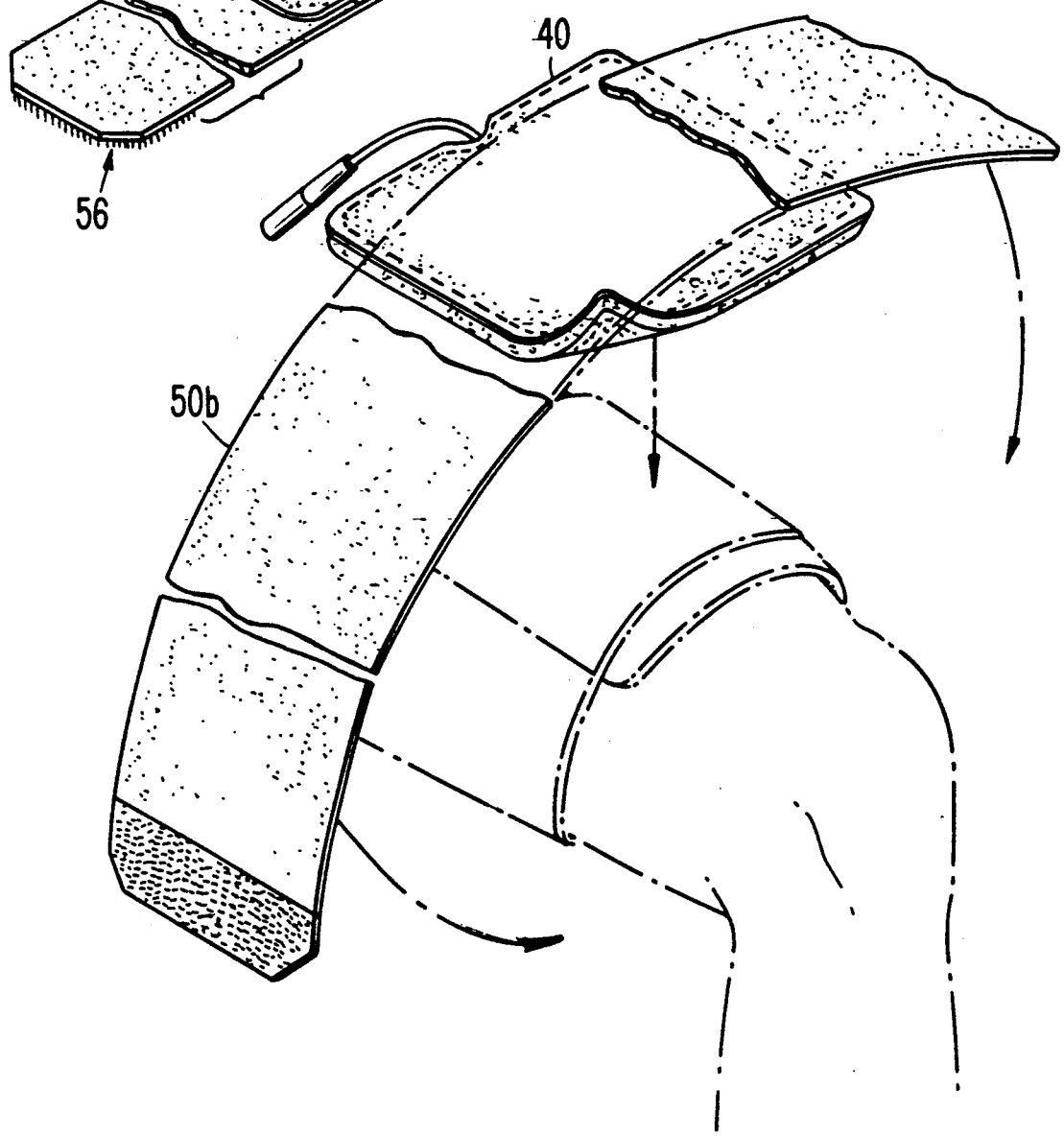
FIG. 3 is a perspective view showing the application of the return pad to the thigh of a patient.

Referring now to FIG. 3, the return pad 40 is supplied to securing wrap 50b in substantially the same manner as electrode pads 30.

To use the pulse galvanic medical treatment device according to the present invention, intensity control 15 is first in the off position. The mode control 14, the rate control 16, and polarity switch 17 are then set as indicated by a clinician. Lead wire connectors 22 are plugged into output jacks 18. The liquid absorbing members 34 and 44 are then moistened with water, and excess water is squeezed out. Next, lead wire connectors 22 are connected to pigtail connectors 32 and 42. Electrode pads 30 are positioned on securing wrap 50a, as shown in FIG. 2. The pads should then be placed over the area to be treated. The securing wrap 50a is then wound around the body part, and starting tab 56 is secured to the surface of inelastic starting portion 52 to hold the electrode pads in place. The fastening tab 58 and the elastic tightening portion 54 are then stretched around the body part and secured to inelastic portion 52 to tighten the wrap. The return pad 40 is then secured over an area indicated by a clinician in a similar manner, as shown in FIG. 3. The intensity control 15 is then turned on and set as indicated by a clinician.

When the electrode pads and return pads are in place, pigtail connectors 32 and 42 may easily be seen by the patient. Also, since the electrical connection is made remote from the moistened pads, the chance of an undesirable electrical shock is reduced.

It should become obvious to those skilled in the art that this invention is not limited to the preferred embodiments shown and described.

What is claimed is:

1. A pulsed galvanic medical treatment device, comprising:
    means for controlling power;
    a plurality of substantially planar pads, including treatment and return pads, said treatment and return pads each having a coating forming a first surface thereof, a liquid absorbing member forming a second surface thereof opposite said first surface, and an electrical conductor disposed between said first and second surfaces;
    a first elongated band adapted to be wrapped around a first part of a body to be treated;
    means for adjustably attaching said treatment pads to said first elongated band;
    connecting means for connecting the electrical conductor of each of said pads to said power control means;
    a second elongated band adapted to be wrapped around a second part of the body to be treated; and
    means for adjustably attaching said return pad to said second elongated band;
    wherein each of said first and second elongated bands has a substantially inelastic starter portion forming a first end portion thereof and adapted to receive said treatment pads and said return pad, respectively, an elastic tightening portion forming a second end portion thereof, and fasteners located on said first and second end portions and adapted to be joined to said inelastic starter portion.

2. The treatment device according to claim 1 wherein said coating is vinyl.

3. The treatment device according to claim 1, wherein said fasteners comprise:
    a first hook and loop fastener portion disposed on said substantially inelastic starter portion; and
    a second hook and loop fastener portion disposed on said elastic tightening portion.

4. The treatment device according to claim 1, wherein said power control means comprises:
    means for selecting the mode of current delivery;
    means for controlling the intensity of the current;
    means for controlling the frequency of the current; and
    means to control the polarity of the planar pad means.

5. The treatment device according to claim 1, wherein said means for adjustably attaching said treatment pads comprises a pair of fasteners disposed along opposite edges of said first surface, so that said treatment pads may be removably and adjustably attached to said first elongated band.

6. The treatment device according to claim 5, wherein said fasteners of said attaching means are hook and loop fasteners.

7. The treatment device according to claim 1, wherein a pair of fasteners are attached to opposite edges of said first surface of each of said treatment and return pads, so that said treatment and return pads may be removably and adjustably attached to the inelastic starter portion of said first and second elongated bands, respectively.

8. The treatment device according to claim 7, wherein said fasteners on said first surface are hook and loop fasteners.

9. The treatment device according to claim 1, wherein said connecting means comprises electrically conducting members connected to the electrical conductor of each of said treatment and return pads.

10. The treatment device according to claim 9, wherein each of said electrically conducting members includes a pigtail connection forming a terminal end thereof, and wherein said connecting means further comprises electrical wires connecting said power control means to said pigtail connections.

11. The treatment device according to claim 10, wherein said pigtail connections are spaced from said treatment and return pads, respectively.

12. A pulsed galvanic medical treatment device, comprising:
    means for controlling power;
    a substantially planar pad having a coating forming a first surface thereof, a liquid absorbing member forming a second surface thereof opposite said first surface, and an electrical conductor disposed between said first and second surfaces;
    an elongated band adapted to be wrapped around a part of a body to be treated;
    means for adjustably attaching said pad to said elongated band; and
    connecting means for connecting the electrical conductor of said pad to said power control means,
    wherein said elongated band has a substantially inelastic starter portion forming a first end portion thereof and adapted to receive said pad, an elastic tightening portion forming a second end portion thereof, and fasteners located on said first and second end portions and adapted to be joined to said inelastic starter portion.

13. The treatment device according to claim 12, wherein said fasteners comprise a first hook and loop fastener portion disposed on said substantially inelastic starter portion, and a second hook and loop fastener portion disposed on said elastic tightening portion.

14. The treatment device according to claim 13, wherein said means for adjustably attaching comprise a pair of hook and loop fasteners attached to opposite edges of said first surface of said pad.

* * * * *